United States Patent [19]
Righi et al.

[11] Patent Number: 5,562,624
[45] Date of Patent: Oct. 8, 1996

[54] NON-REUSABLE SAFETY SYRINGE

[76] Inventors: Nardino Righi, 117, Viale Lombardia, I-20093 Cologno Monzese, Province of Milano; Roberto Rossi, 10, Via delle Ande, I-20151 Milano, both of Italy

[21] Appl. No.: 241,448

[22] Filed: May 11, 1994

[51] Int. Cl.$^6$ .................................................. A61M 5/00
[52] U.S. Cl. ............................ 604/110; 604/198; 604/263
[58] Field of Search .................................. 604/110, 198, 604/192, 187, 263, 218

[56] References Cited

U.S. PATENT DOCUMENTS

| | | | |
|---|---|---|---|
| 5,163,918 | 11/1992 | Righi et al. | 604/198 |
| 5,201,708 | 4/1993 | Martin | 604/110 |
| 5,259,841 | 11/1993 | Hohendorf et al. | 604/110 |

Primary Examiner—John D. Yasko
Attorney, Agent, or Firm—Larson and Taylor

[57] ABSTRACT

A non-reusable safety syringe comprising a cylinder (1); an injection needle (4) fixed on the front end of the cylinder (1); a plunger (6) which is slidable in the cylinder (1) from a position of maximum withdrawal for the filling of the syringe to a position of maximum insertion for the discharging of the syringe, and which is mounted on a manually movable stem (7) which projects beyond the rear end of the cylinder (1); a protective sleeve (12) fitted slidably longitudinally on the outside of the cylinder (1) so that it can be moved from a withdrawn inoperative position, in which the needle (4) projects beyond it, to a forward safety position, in which the protective sleeve (12) extends entirely around the needle (4), covering it completely, and with securing means (23, 25) to automatically retain the protective sleeve (12), so that it cannot be retracted with respect to the cylinder (1), in its forward safety position and the needle-holder (3) in the protective sleeve (12) in its forward position.

15 Claims, 5 Drawing Sheets

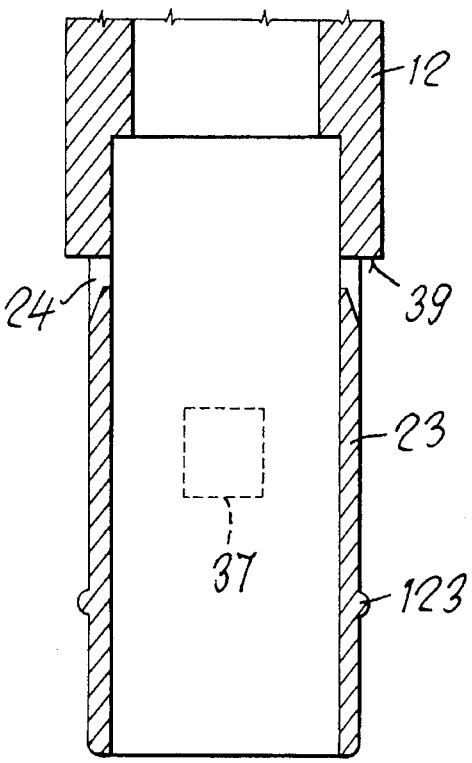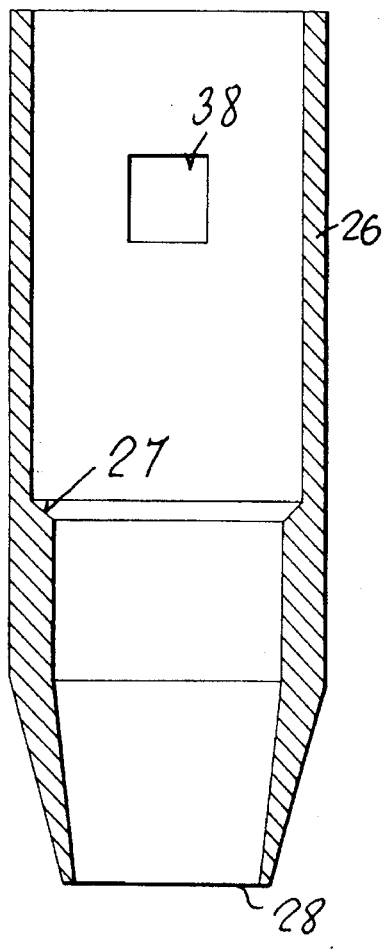
Fig. 3

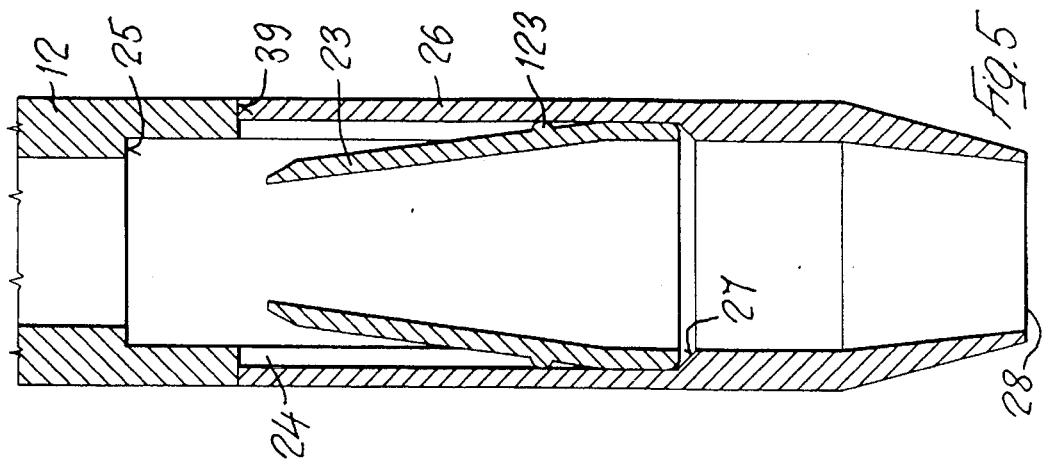
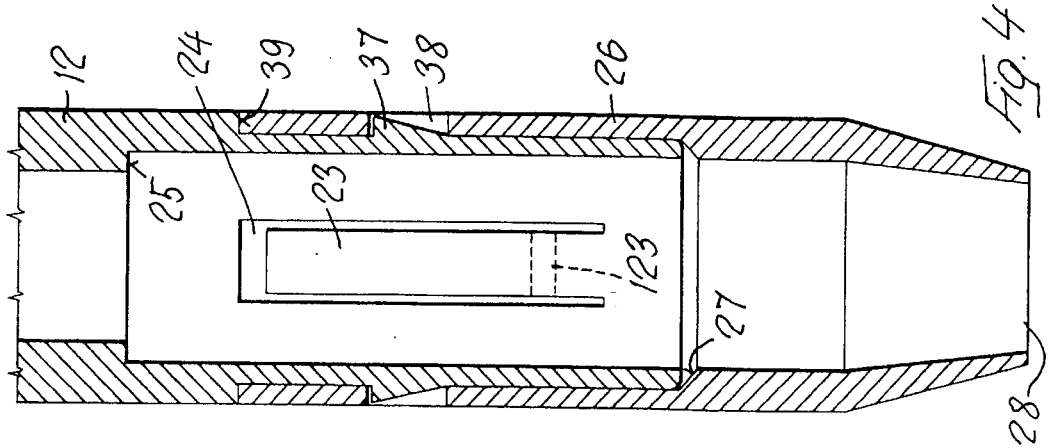
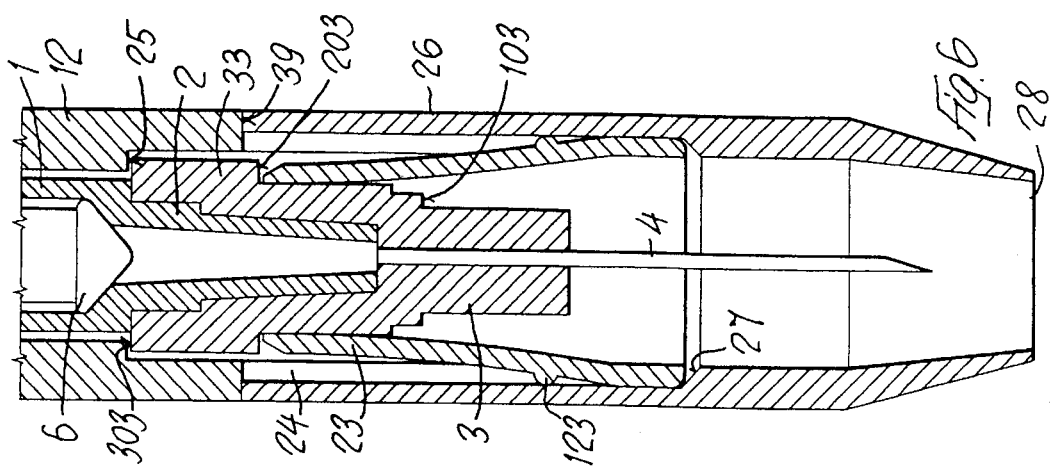

NON-REUSABLE SAFETY SYRINGE

The present invention relates to a syringe which is non-reusable, and which consequently acts as a safety syringe.

More specifically, the invention relates to a non-reusable safety syringe comprising:

a) a cylinder;

b) a needle which is fixed to a needle-holder, which is fitted removably in and/or on the front end of the cylinder;

c) a plunger which is slidable in the cylinder from a position of maximum withdrawal for the filling of the syringe to a position of maximum insertion for the discharging of the syringe, and which is provided with a manually movable stem which projects beyond the rear end of the cylinder;

d) a protective sleeve fitted slidably on the outside of the cylinder and so that it can be moved from a withdrawn inoperative position, in which the needle projects beyond the sleeve, to a forward safety position, in which the protective sleeve extends entirely around the needle, covering it completely;

e) hooked securing teeth which are provided at the free rear ends of elastically flexible securing tongues extending longitudinally with respect to the protective sleeve, the tongues being formed in one piece with the sleeve, while the securing teeth interact with a complementary retaining rim on the rear end of the cylinder to secure the protective sleeve in its withdrawn position with respect to the cylinder;

f) a releasing pusher element which is fixed to the rear end of the stem of the plunger and which interacts with the securing teeth to disengage the said teeth from the retaining rim on the rear end of the cylinder, in the terminal section or substantially in the terminal section of the insertion path of the plunger;

g) a spring which is interposed between the cylinder and the protective sleeve and which is designed to move the protective sleeve from its withdrawn inoperative position to its forward safety position;

h) two removal prevention teeth which are disposed diametrically opposite each other at the rear end of the cylinder and which can be moved elastically radially outwards away from each other, and can interact with the rear side of the releasing pusher element, securing the stem of the plunger in the maximum insertion position of the path of the plunger;

i) removable safety means which are provided at the rear end of the cylinder, to prevent the releasing pusher element from interacting with the securing teeth;

j) securing means which are capable of automatically retaining both the protective sleeve in its forward safety position, so that it cannot be withdrawn with respect to the cylinder, and the needle-holder so that it cannot be removed axially in either direction from the said protective sleeve in its forward safety position, and which consist of at least one internal projection in the protective sleeve for retention at the rear of the needle-holder which interacts with a corresponding external projection on the needle-holder itself, and of at least one elastic front retaining tongue on the needle-holder, which is formed by cutting the peripheral wall of the protective sleeve and which extends longitudinally with respect to the sleeve, its rear end being connected to the protective sleeve, while its free rear end interacts, in a position of radial entry into the protective sleeve, with a corresponding front projection of the needle-holder.

In known syringes of this type, the retaining tongue or tongues of the protective sleeve are formed during manufacture with their free ends already inclined radially towards the inside of the sleeve, while they yield elastically towards the outside. This requires a relatively complex and costly process of manufacturing the protective sleeve, accompanied by an undesirable increase in the cost of the syringe.

The object of the present invention is to provide a non-reusable safety syringe of the type described initially which is of simpler and more economical design, but is equally reliable and safe in operation, particularly as regards the protective sleeve.

The present invention achieves the object with a non-reusable safety syringe of the type described initially, in which the retaining tongue or tongues are cut in the front terminal section of the protective sleeve so that they extend initially, in the unstressed condition, substantially coplanar with the peripheral wall of the sleeve, while they interact with an end cap which reduces the front hole for the needle which may be fitted over and secured removably to the end of the protective sleeve, so that the tongue or tongues are compressed radially inwards in an inclined position with their ends projecting inside the sleeve.

According to one particularly simple embodiment, a projection interacting with the inner surface of the end cap is provided on the outer side of the retaining tongue or tongues. Alternatively, the projection may be provided on the inner surface of the end cap.

As a result of the arrangements described above, the protective sleeve may be formed in an extremely simple and inexpensive way, for example by a simple procedure of moulding or similar.

The present invention has further characteristics which are described in the subsidiary claims.

The characteristics of the invention and the advantages derived therefrom will be more clearly understood from the following description of one embodiment, illustrated in the attached drawings, in which:

FIG. 3 is a longitudinal sectional disassembled view of the terminal part of the protective sleeve and of the end cap to be fitted over it;

FIGS. 4 and 5 are longitudinal sectional views in two mutually orthogonal planes of the end part of the protective sleeve with the end cap fitted on it;

FIG. 6 is a view similar to FIG. 5, with the protective sleeve in the forward safety position with respect to the cylinder of the syringe and with the needle-holder in the position in which it is secured in the corresponding front end of the protective sleeve.

Figure 1:
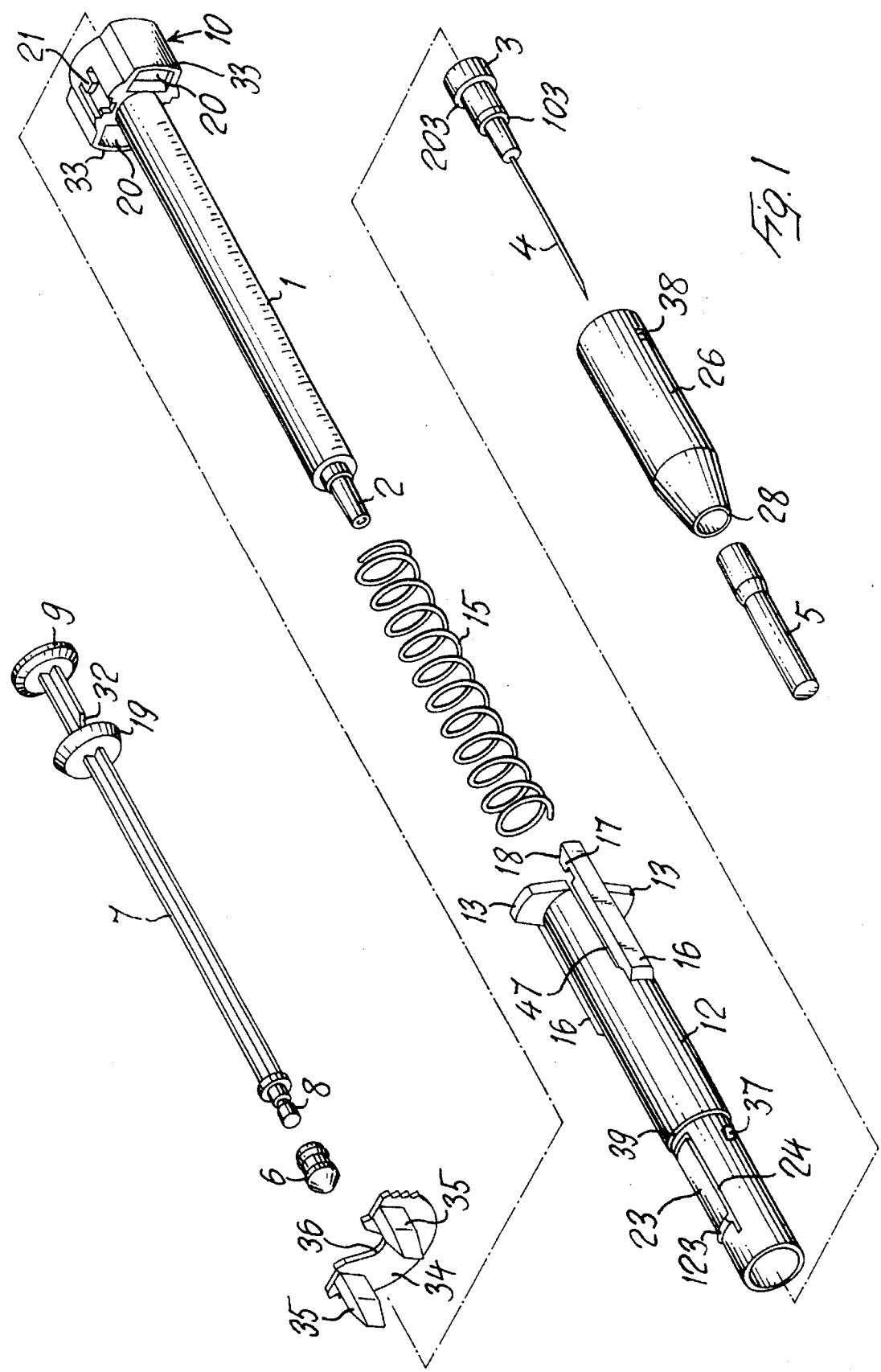
FIG. 1 is an exploded perspective view of an embodiment of the syringe according to the invention.

In the following description and in the attached claims, the expression "front end of the syringe" denotes the end of the syringe to which the needle is fixed, while the rear end of the syringe is its opposite end from the needle. Additionally, when not specified otherwise, all the elements of the syringe, with the exception of the needle, are preferably made of a suitable plastic material or similar.

With reference to the embodiment shown in FIGS. 1 to 6, the non-reusable safety syringe comprises a cylinder 1, with a conical front end 2 on which is fitted the needle-holder 3 which is retained by a frictional connection using a complementary conical hole formed in the rear end of the needle-holder, while the rear end of the needle 4 is incorporated stably in the hole. Normally, the needle 4 is protected by a needle cover cap 5 which is engaged removably with the front end of the needle-holder 4 so that it bears on a step 103 provided on the end. A plunger 6 is axially movable in a fluid-tight way in the cylinder 1, and the head 8 of the manually movable stem 7 is engaged in the plunger 6. The rear terminal section of the stem 7 extends to the rear outside the cylinder 1 and is provided with a push-button 9 on its rear end. The stem 7 preferably has a non-circular cross-section which may be, for example, in the shape of a T or an X. The rear terminal section of the cylinder 1 is enlarged so that a generally cylindrical can-shaped head 10 is formed, with two radial enlargements diametrically opposite each other.

A protective sleeve 12 is fitted externally on the cylinder 1 so that it can slide longitudinally on the cylinder. Two diametrically opposite fins 13 are formed on the rear end of the protective sleeve 12 and extend radially from the peripheral surface of the sleeve. A metal spiral spring 15 is interposed between an internal step 14, provided in the protective sleeve 12 at a certain distance from its rear end, and the can-shaped head 10 of the cylinder 1.

At its rear end, the protective sleeve 12 is provided with two securing tongues 16 formed in one piece with it and disposed in two positions diametrically opposite each ocher. Each securing tongue 16 extends longitudinally with respect to the protective sleeve 12, in a longitudinal slot 47 made in the sleeve. The front end of the tongue 16, in other words its end nearer the needle 4, is connected to the protective sleeve 12, while its rear end extends beyond the rear end of the protective sleeve 12, projecting outside the rear end of the sleeve. Each securing tongue 16 may be elastically bent outwards in the radial direction and its rear end consists of a securing tooth 17 in the form of a hook which is turned radially inwards. Additionally, each securing tongue 16 is provided, at the rear end of its securing tooth 17, with an inclined guide surface 18 which is inclined downwards towards the inside, and is designed to interact with the correspondingly inclined lateral peripheral edge of a discord pusher element 19 fixed on the stem 7 of the plunger 6 to the rear of the can-shaped head 10 of the cylinder 1 opposite the securing tongue 16.

The can-shaped head 10 at the rear end of the cylinder 1 has a lateral wall 33 which radially and externally covers the rear free ends of the securing tongues 16, which form the hooked securing teeth 17 which are designed to penetrate into the can-shaped head 10 through the apertures 20 in its end. Each securing tongue 16 can therefore penetrate into the can-shaped head 10 and its corresponding securing tooth 17 in the form of a hook can engage with the end of the head 10. Cuts made in the lateral wall of the can-shaped head 10 provide removal prevention teeth 21 which are disposed at angles of 90° with respect to the two apertures 20 for the securing tongues 16. The removal prevention teeth 21 can be moved elastically radially outwards away from each other, and have opposing inner sides consisting of guide surfaces which are inclined inwards and downwards, and are designed to interact with the correspondingly inclined lateral peripheral edge of the discord pusher element 19.

The front part of the protective sleeve 12 carries a tubular element 26 in the form of an end cap. The end cap 26 has a conically tapering front hole 28 which is only slightly larger than the rear terminal part of the needle cover cap 5. The end cap 26 is fitted externally on the protective sleeve 12 and is permanently engaged with the sleeve by a catch. The protective sleeve 12 is thus provided with a front terminal section of reduced diameter, on which the end cap 26 is fixed so that it bears on an annular external constricting step 39 formed on the protective sleeve 12. The protective sleeve 12 is secured in position by two external retaining projections 37 which are provided in positions diametrically opposite each other on the outside of the protective sleeve 12 and which engage as catches in two corresponding slots 38 in the end cap 26. With the end cap 26 in its engaged position, the end cap 26 bears with an internal annular shoulder 27—an internal conical constriction in the example—on the edge of the front end of the protective sleeve 12 as illustrated in greater detail in FIGS. 4 to 6.

Two retaining tongues 23 diametrically opposite each other are provided in the front section of the protective sleeve 12, and are formed in the protective sleeve 12 by means of a cut 24 made in the sleeve. Each retaining tongue 23 extends longitudinally with respect to the protective sleeve 12. As shown in FIGS. 1 and 3, initially, in other words in the absence of the end cap 26, the retaining tongues are in an unstressed condition and extend so that they are generally coplanar with the lateral wall of the protective sleeve 12. The front end of each retaining tongue 23 is connected to the protective sleeve 12, while the rear end of the tongue is free. The retaining tongues 23 may be inclined elastically radially inwards, so that their free rear ends are brought into a position where they project inside the protective sleeve 12 by means of external projections 123 provided on the outer sides of the tongues and interacting with the end cap 26 when it is fitted on the protective sleeve 12. The external projections 123 are provided on the front end sections of the retaining tongues 23 connecting them to the protective sleeve 12. This enables the tongues to be bent elastically radially outside the cylinder 1, in the withdrawn inoperative condition of the protective sleeve 12, as shown in FIG. 2.

This situation is illustrated in detail in FIGS. 3 to 6, and enables the protective sleeve 12 to be made in an extremely simple and economical way, in particular by an injection moulding process with the use of simple and inexpensive moulds.

Figure 2:
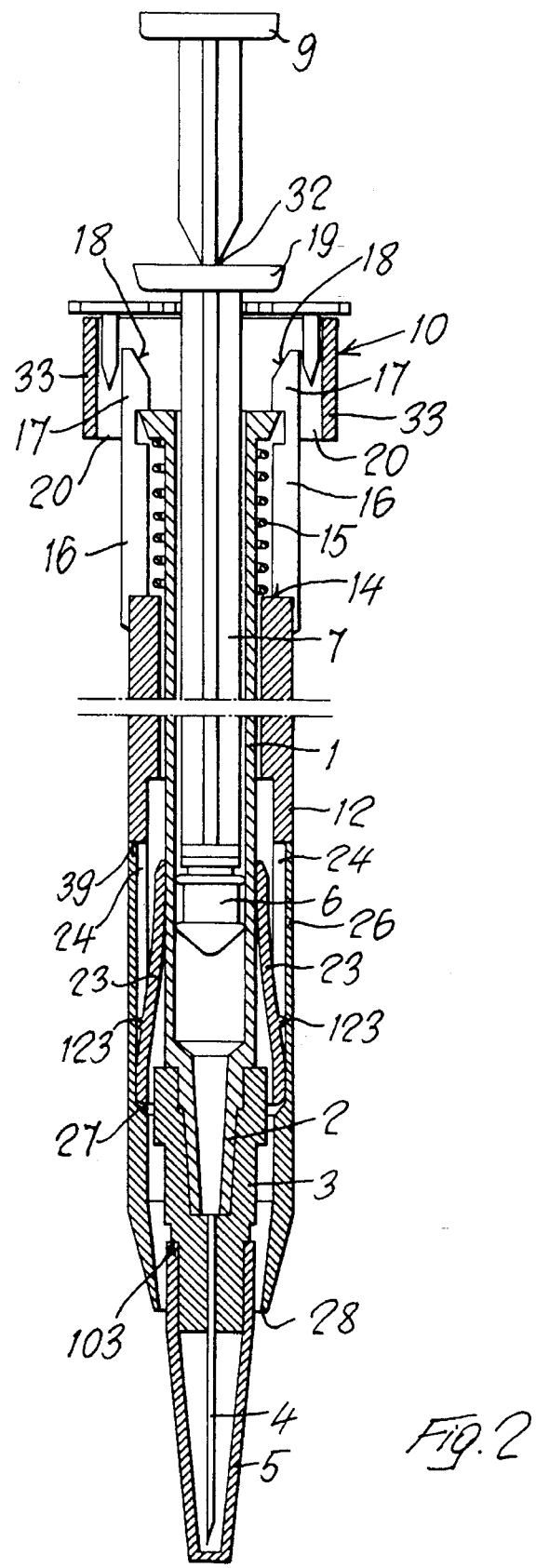
FIG. 2 is a longitudinal sectional view of the syringe according to FIG. 1, with the protective sleeve in its withdrawn position.

As shown in FIGS. 2 and 6, the free rear ends of the retaining tongues 23 are designed to interact with an external peripheral shoulder 203 of the needle-holder 3. The protective sleeve 12 has, at a certain distance from the retaining tongues 23 towards the rear end of the syringe, an internal retaining projection 25, which may be made in the form of an annular shoulder and whose front end may consist of a plurality of ribs (not illustrated) provided inside the protective sleeve 12. The internal protective projection 25 is designed to interact with the peripheral annular part 33 of the edge of the rear end of the needle-holder 3. The needle-holder 3 which is fixed stably on the front end 2 of the cylinder 1 projects beyond the peripheral surface of the cylinder 1 with the peripheral part of its edge on the rear end, in such a way as to form an external annular step 303, which is associated with the internal retaining projection 25 in the protective sleeve 12.

The syringe is sold to the user in the condition shown in FIG. 2, in which the plunger 6 is slightly withdrawn from its maximum insertion position in which the syringe is completely discharged. In this condition of the syringe, the discord pusher element 19 is disposed slightly outside the can-shaped head 10 at the rear end of the cylinder 1, while it is prevented from penetrating into the head by removable safety means.

The removable safety means for initially preventing the entry of the discord pusher element 19 into the can-shaped head 10 at the rear end of the cylinder 1 consist of a small covering element 34 in the general form of a sector of a circle, which has a central aperture 36 to allow the stem 7 to pass through it. In place of the element 34, it is also possible to provide a removable tear-off strip of paper or cardboard, which is not illustrated. The small covering element 34 is fitted on the aperture towards the rear end of the can-shaped head 10 and for this purpose is provided with two wedge-shaped teeth 35 diametrically opposite each other on the front side facing the front end of the syringe. The teeth 35, which extend from the covering element 34, are inserted in the aperture in the rear end of the can-shaped head 10 so that they penetrate between the two securing tongues 16, whose hooked securing teeth 17 are engaged with the end of the can-shaped head 10, and the corresponding parts of the lateral wall 33 of the head. In this way the two teeth 35 hold the covering element in position on the can-shaped head 10 at the rear end of the cylinder 1 and simultaneously prevent the rear free ends of the securing tongues 16 from being bent radially outwards and consequently from being disengaged from the can-shaped head 10. The covering element 34 partially covers the aperture of the can-shaped head 10 at the rear end of the cylinder 1 and thus prevents the discord pusher element 19 from penetrating into the head 10.

Before the syringe is used for an injection, the covering element 34 must be removed. To do this, the user of the syringe must take hold of the covering element 34 with two fingers of his hand on two diametrically opposite points, preferably toothed, of the peripheral edge of the covering element, in such a way as axially to disengage the covering element 34 from the can-shaped head 10 at the rear end of the cylinder 1, and then move it radially away from the stem 7 of the plunger 6.

The protective sleeve is disposed in its withdrawn inoperative position, in which the securing tongues 16 are designed to penetrate into the can-shaped head 10 of the cylinder 1 through the apertures 20. The hooked securing teeth 17 of the securing tongues 16 are therefore engaged with the end of the said head 10, fixing the protective sleeve 12 to the cylinder 1. With the protective sleeve 12 in its withdrawn inoperative position, the spring 15 is stressed, in other words compressed, and the fins 13 which extend radially from the peripheral surface of the protective sleeve 12 bear on or almost bear on the front side of the can-shaped head 10 of the cylinder 1. Additionally, when the protective sleeve 12 is in its withdrawn inoperative position, the constricted front section of the end cap 26 extends substantially as far as the front end of the needle-holder 3, so that the needle 4 is left uncovered in a projecting position, when the needle cover cap 5 is removed in a forward direction. The internal diameter of the hole 28 is slightly greater than the diameter of the needle cover 5, in other words than of the complementary terminal part which is therefore disposed in a position very close to the front end of the end cap 26. In the aforesaid condition of the syringe according to FIG. 2, the plunger 6 may be freely extracted by drawing its stem 7 backwards, so that the cylinder 1 is filled in the usual way by suction through the uncovered needle 4 of the liquid to be injected. The diameter of the hole 28 is also smaller than the diameter of the external peripheral shoulder 203 of the needle-holder 3, so that it becomes effectively impossible to remove the needle-holder 3 from the front ends of the cylinder 1 and of the protective sleeve 12 when this is in its withdrawn inoperative position.

In order to give the injection, it is necessary to remove the covering element 34, while the syringe is held by two fingers of the user's hand each placed on the front of the corresponding fin 13 which extends radially from the peripheral surface of the rear end of the protective sleeve 12, while the plunger 6 is pressed forwards by the user's thumb which is placed on the push-button 9 of the stem 7 of the plunger. In the terminal section of the insertion path of the plunger 6, the discord pusher element 19 penetrates into the can-shaped head 10 of the cylinder 1 through the aperture in its rear end, while its peripheral lateral edge bears on the inclined guide surfaces 18 of the securing tongues 16. Consequently, the securing tongues 16 are moved elastically outwards away from each other so that their hooked securing teeth 17 are disengaged from the end of the can-shaped head 10 of the cylinder 1. The protective sleeve 12 is thus released from the cylinder 1, but remains retracted in its withdrawn inoperative position against the action of the pressure spring 15 while it is held by the operator's hand in the way described above. Before and/or at the moment when the securing tongues 16 are opened outwards as indicated above, the peripheral lateral edge of the discord pusher element 19 acts against the inclined guide surfaces of the removal prevention teeth 21, passing beyond them. The teeth 21 are thus moved elastically apart so that they become engaged with a snap fit with the upper side of the discoid pusher element 19. Consequently, when the injection is given, the pusher element 19 is secured in the can-shaped head 10 of the cylinder 1 at the end or approximately at the end of the introduction path of the plunger 6, between the end of the head 10 and the removal prevention teeth 21, in such a position that the securing tongues 16 are kept in their mutually distant position, and the protective sleeve 12 is thus disengaged from the cylinder 1.

After the injection has been given, the peripheral radial fins 13 which extend radially from the rear end of the protective sleeve 12 are released, by the user as a result of which the protective sleeve, which is now disengaged from the cylinder 1, is moved forwards by the spring 15, either gradually or all at once, into its forward safety position. As illustrated in FIG. 6, in its forward safety position the protective sleeve extends around the needle 4 so as to cover it completely. The internal retaining projection 25 of the protective sleeve 12 simultaneously comes to bear on the rear annular step 303 formed by the peripheral area of the edge of the rear end of the needle-holder 3, while the free rear ends of the securing tongues 23 which are inclined radially into the protective sleeve 12 by the end cap 26 and the external projections 123 on them come to bear simultaneously on the external annular shoulder 203 of the needle-holder 3. Thus in its forward safety position the protective sleeve is secured permanently to the cylinder 1, in both longitudinal directions, in other words in the direction of advance and in the direction of withdrawal, by means of the needle-holder 3. When a person attempts to remove the protective sleeve 12 forwards from the cylinder 1, in an attempt to re-use the syringe, in the worst case the needle-holder 3 is removed from the conical front end of the cylinder 1 so that the protective sleeve 12 becomes detached from the cylinder 1 together with the needle-holder 3 which is enclosed inseparably in the protective sleeve 12 and is therefore retained in the protective sleeve 12 together with the needle 4. The protective sleeve 12 may be made in an uncomplicated way and inexpensively from a plastic material which is sufficiently robust and strong to make it impossible to break the protective sleeve without damaging and rendering unusable the needle-holder 3 and also the needle 4. Additionally, the end cap 26 on the protective sleeve 12 has a hole 28 which is so small and extends for such a distance beyond the point of the needle 4 that it is impossible for a person's finger to reach the needle 4 from the front end of the syringe.

The stem 7 of the plunger 6 may be provided with a weakened area 32 which is easily breakable at a point between the discord pusher element 19 and the push-button 9 on the rear end of the stem 7, preferably at a point adjacent to the discord pusher element 19. When such a weakened area is provided, the rear terminal section of the stem 7 breaks when an attempt is made to draw the plunger 6 backwards in an attempt to re-use the syringe, once the discord pusher element 19 has been secured in the can-shaped head 10 of the cylinder 1 by means of the removal prevention teeth 21.

The protective sleeve 12 may be fitted slidably but not rotatably on the cylinder 1 with the aid of simple means known to experts in the art, for example an internal projection in the sleeve 12 which is engaged slidably in a longitudinal groove on the outside of the cylinder 1, or vice versa.

Figure 7:
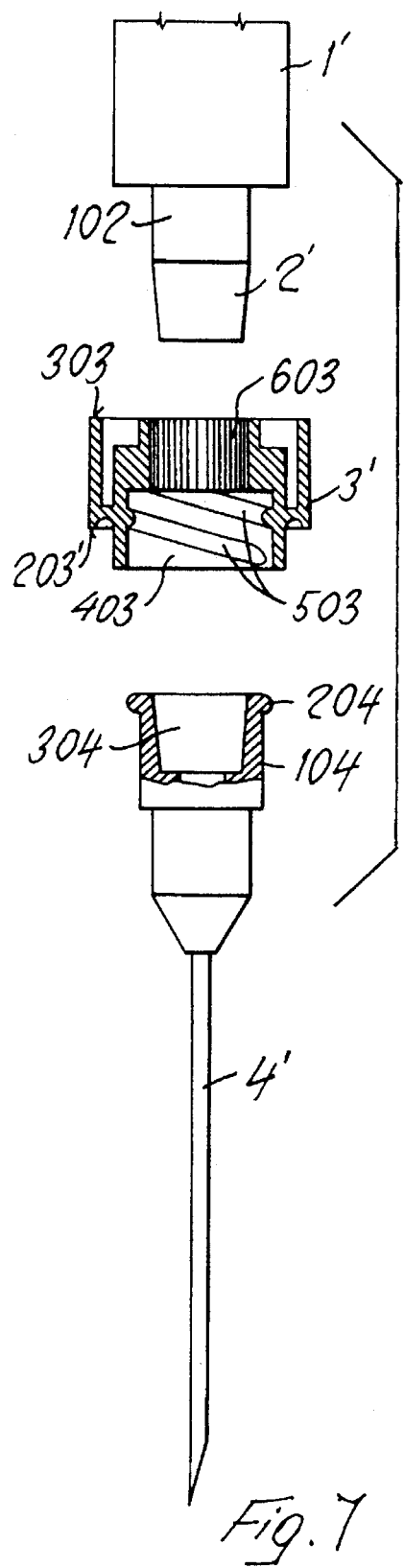
FIG. 7 is a longitudinal sectional view of an alternative embodiment of the needle-holder, particularly shaped for using conventional needles.
Figure 8:
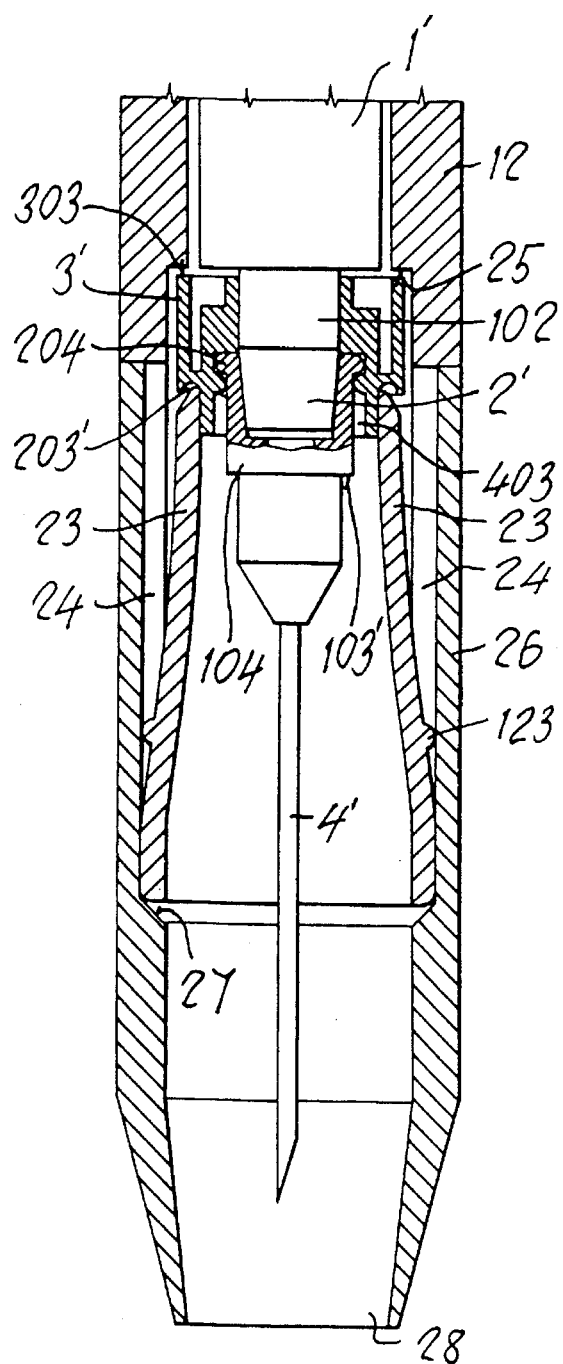
FIG. 8 is a longitudinal sectional view of the needle and the needle-holder according to FIG. 7 in the position in which the needle-holder is secured in the corresponding front end of the protective sleeve.

According to FIGS. 7 and 8, for using a conventional needle 4', the needle-holder 3' is built as a separate, intermediate, bushing shaped element and shows on its needle fixing side a needle-fixing hole 403 with an internal multi-start screw thread, particularly a double-start screw thread 503, in which a needle securing head 104 of a conventional needle 4' can be screwed by means of an external peripheral flange 204 on the needle securing head 104 itself.

The needle-fixing hole 403 prolongs itself to the side of the needle-holder 3' facing the cylinder 1' with a coaxially narrowed cylindrical extension 603, having a diameter substantially corresponding to the diameter of a cylindrical part 102 connecting the conical frontal end 2' of the syringe to the cylinder 1 and on which extension 603 this cylindrical part 102 can be fitted, while the conical front end 2' engages a complementary conical hole 304 in the needle securing head 104, providing also the necessary seal. The narrowed extension 603 also forms an inner annular shoulder against which the flange 204 of the needle securing head 104 is screwed.

Advantageously, the cylindrical extension 603 can show axially oriented internal readings, an internal ring gear, or the like, for providing stronger fitting on the cylindrical part 102.

As a further improvement, the external peripheral shoulder 203' of the needle-holder 3' cooperating with the retaining tongues 23 shows a concave surface, as an annular groove or the like.

We claim:

1. Non-reusable safety syringe comprising:

a) a cylinder (1) having a front end and a rear end;

b) a needle (4) which is fixed to a needle-holder (3), which is fitted removably to the front end of the cylinder (1);

c) a plunger (6) which is slidable in the cylinder (1) from a position of maximum withdrawal for the filling of the syringe to a position of maximum insertion for the discharging of the syringe, and which is provided with a manually movable stem (7) which projects beyond the rear end of the cylinder (1);

d) a protective sleeve (12) fitted slidably on the outside of the cylinder (1) and so that it can be moved from a withdrawn inoperative position, in which the needle (4) projects beyond the sleeve (12), to a forward safety position, in which the protective sleeve (12) extends entirely around the needle (4), covering the needle (4) completely;

e) hooked securing teeth (17) which are provided at free rear ends of elastically flexible securing tongues (16) extending longitudinally with respect to the protective sleeve (12), the tongues being formed in one piece with the sleeve (12), while the securing teeth (17) interact with a complementary retaining rim on the rear end of the cylinder (1) to secure the protective sleeve (12) in its withdrawn position with respect to the cylinder (1);

f) a releasing pusher element (19) which is fixed to a rear end of the stem (7) of the plunger (6) and which interacts with the securing teeth (17) to disengage said teeth from the retaining rim on the rear end of the cylinder (1), substantially in a terminal section of an insertion path of the plunger (6);

g) a spring (15) which is interposed between the cylinder (1) and the protective sleeve (12) and which is designed to move the protective sleeve (12) from its withdrawn inoperative position to its forward safety position;

h) two removal prevention teeth (21) which are disposed diametrically opposite each other at the rear end of the cylinder (1) and which can be moved elastically radially outwards away from each other, and can interact with a rear side of the releasing pusher element (19), securing the stem (7) of the plunger (6) in the maximum insertion position of the path of the plunger (6);

i) removable safety means (34) which are provided at the rear end of the cylinder (1), to prevent the releasing pusher element (19) from interacting with the securing teeth (17); and j) securing means which are capable of automatically retaining both the protective sleeve (12) in its forward safety position so that it cannot be withdrawn with respect to the cylinder (1) and the needle-holder (3) so that it cannot be removed axially in either direction from said protective sleeve (12) in its forward safety position, and which consist of at least one internal projection (25) in the protective sleeve (12) for retention at a rear of the needle-holder (3) which interacts with a corresponding external projection (303) on the needle-holder (3) itself, and of at least one elastic front retaining tongue (23) on the needle-holder (3), which is formed by cutting a peripheral wall of the protective sleeve (12) and which extends longitudinally with respect to the sleeve, a front end of said retaining tongue being connected to the protective sleeve (12), while a free rear end of said retaining tongue interacts, in a position of radial entry into the protective sleeve (12), with a corresponding front projection (203) of the needle-holder (3);

characterized in that the at least one retaining tongue (23) is cut in a front terminal section of the protective sleeve (12) so as to extend initially, in an unstressed condition, substantially coplanar with the peripheral wall of the protective sleeve, while the at least one retaining tongue interacts with an end cap (26) which reduces a front hole (28) for the needle (4) which may be fitted over and secured removably to an end of the protective sleeve (12), so that the tongue (23) is compressed radially inwards in an inclined position with the end of the retaining tongue projecting inside the protective sleeve (12); and further characterized in that an external projection (123) interacting with an inner surface of the end cap (26) is provided on an outer side of the retaining tongue (23) to cause a radial inclination of the retaining tongue (23) towards an inside of the sleeve (12) when the end cap (26) is fitted onto the sleeve (12).

2. Syringe according to claim 1, characterised in that internal projections project from the inner surface of the end cap (26) and are provided at positions coinciding with the retaining tongue or tongues (23) and interact with the tongues to bend them radially towards the inside of the protective sleeve (12) when the end cap (26) is fitted onto the sleeve.

3. Syringe according to claim 1, characterised in that the external projections (123) of the retaining tongues (23) or the internal projections of the end cap (26) are provided in positions coinciding with the front end sections of the retaining tongues (23) connecting them to the protective sleeve (12).

4. Syringe according to claim 1, characterised in that two securing tongues (16) diametrically opposite each other and with inclined guide surfaces (18) facing each other and interacting with the releasing pusher element (19) are provided.

5. Syringe according to claim 1, characterised in that the removal prevention teeth (21) are formed by cuts made in the lateral wall of a can-shaped head (10) made in one piece with the rear end of the cylinder (1), while the securing tongues (16) which project from the rear end of the protective sleeve (12) extend with their free rear ends, which consist of hooked securing teeth (17) and inclined guide surfaces (18), into the said can-shaped head (10), passing through corresponding apertures (20) made in the end of the said head (10), while the locking edge at the rear end of the cylinder (1) consists of the edges of the said apertures with which the said securing teeth (17) engage, the can-shaped head (10) being made with an aperture on its rear end to enable the disc-shaped releasing pusher element (19), which is fixed to the rear terminal section of the stem (7) of the plunger (6), to penetrate into the said head (10).

6. Syringe according to claim 1, characterised in that the removable safety means are made in the form of a covering element (34) which is provided with a radial cut (36) to allow the stem (7) of the plunger (6) to pass through it and which can be fitted to the aperture in the rear end of the can-shaped head (10) of the cylinder (1) by means of extensions (35) which are inserted into the said head (10) and which are designed to interact with the securing tongues (16) in such a way as to prevent the said tongues from being bent into their release position, the said covering element (34) being disposed between the pusher element (19) and the rear end of the can-shaped head (10).

7. Syringe according to claim 1, characterised in that the removable safety means may consist of a removable tear-off strip of paper or cardboard, disposed between the pusher element (19) and the rear end of the can-shaped head (10).

8. Syringe according to claim 1, characterised in that, in its withdrawn inoperative position, the protective sleeve (12) bears axially on a stop (10) provided on the rear end of the cylinder (1), while at its rear end the said sleeve has formed on it at least two radial diametrically opposite fins (13) which extend from the peripheral surface of the sleeve and which are to be held by two fingers of the hand of the user who holds the syringe during the injection.

9. Syringe according to claim 1, characterised in that, in its withdrawn inoperative position, the protective sleeve (12) is disposed with its front end (28) next to the rear end of the needle cover cap (5) which is fitted removably on the front end of the needle-holder (3), while the internal diameter of the front hole (28) on the front section of the protective sleeve (12) is constricted with respect to the internal diameter of the remaining part of the said sleeve (12) and is only slightly greater than the external diameter of the complementary rear terminal part of the needle cover cap (5).

10. Syringe according to claim 1, characterised in that the constricted front hole (28) of the protective sleeve (12) is formed by the front hole of the end cap (26) which is fitted permanently by catches onto the protective sleeve (12).

11. Syringe according to claim 1, characterised in that the external shoulder (203) of the needle-holder (3) has a diameter greater than the hole (28) in the end cap (26) at the front end of the protective sleeve (12) and forms a stop to prevent the removal of the said needle-holder (3) from the cylinder (1) and from the protective sleeve (12) in the withdrawn inoperative position of the sleeve.

12. Syringe according to claim 1, characterised in that the stem (7) of the plunger (6) is provided with an easily breakable weakened area (32) at a point between the pusher element (19) and a push-button (9) on the rear end of the stem (7).

13. Syringe according to claim 1, characterized in that, the needle-holder (3) is built as a separate, intermediate element with coupling means (603) to the frontal end (2, 102) of the cylinder (1) and means (403) for engaging a securing head (104, 204) of a conventional needle (4).

14. Syringe according to claim 1, characterized in that the needle-holder (3) is provided with a hole (403) having an internal multi-start, particularly double-start, screw thread (503), in which an external peripheral flange (204) of the needle securing head (104) is screwable.

15. Syringe according to claim 1, characterized in that the needle-holder (3) is built in such a way that the needle securing head (104) engages with a conical hole (304) the conical front end (2) of the cylinder (1), providing the necessary seal.

* * * * *